United States Patent [19]

Yokoi et al.

[11] Patent Number: 5,008,419

[45] Date of Patent: Apr. 16, 1991

[54] NOVEL PLATINUM COMPLEX

[75] Inventors: Koichi Yokoi, Kashiwa; Kazuhiko Irinoda, Chiba; Hidehiko Kohya, Narita; Susumu Sato, Shisui; Tatsuhiko Katori, Tone, all of Japan

[73] Assignee: SS Pharmaceutical Co., Ltd., Tokyo, Japan

[21] Appl. No.: 451,637

[22] Filed: Dec. 18, 1989

[30] Foreign Application Priority Data

Dec. 27, 1988 [JP] Japan .................. 63-330251

[51] Int. Cl.$^5$ .................................. C07F 9/68
[52] U.S. Cl. ........................ 556/137; 556/40
[58] Field of Search ..................... 556/137, 40

[56] References Cited

U.S. PATENT DOCUMENTS 4,169,846 10/1979 Kidani et al. ............... 556/137
4,861,905 8/1989 Nowatari et al. ............ 556/40

FOREIGN PATENT DOCUMENTS 0147926 10/1984 European Pat. Off. .
2423473 4/1979 France .
61-255943 10/1986 Japan .

Primary Examiner—Arthur C. Prescott
Attorney, Agent, or Firm—Oblon, Spivak, McClelland, Maier & Neustadt

[57] ABSTRACT

A platinum complex having the following formula (I) is disclosed,

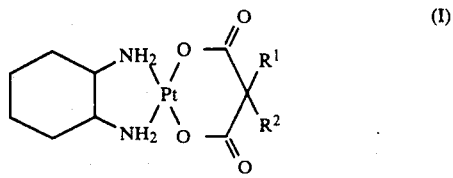

wherein $R^1$ and $R^2$ may be the same or different and each independently represents a methyl group or an ethyl group, and the configuration of 1,2-diaminocyclohexane is either cis-, trans-l-, trans-d-, or trans-dl-.

The compound possess excellent antitumor activity with a high therapeutic index and abundant water solubility, and thus are effective as an antitumor agent.

2 Claims, No Drawings

PLATINUM COMPLEX

BACKGROUND OF THE INVENTION

1. Field of the Invention

This invention relates to a platinum complex having an antitumor activity and to an antitumor agent comprising the same as an effective component.

2. Description of the Background

Cisplatin, which is a platinum complex reported by Rosenberg et al. as a novel antitumor agent in 1969 [Nature, 222, 385 (1969)] has a wide antitumor spectrum and is used especially as an antitumor agent exhibiting a remarkable effect particularly on genitalia cancer, bladder cancer, head and neck cancer, or the like. There are a number of studies on platinum complexes exhibiting antitumor activities other than cisplatin. Among these platinum complexes those having 1,2-diaminocyclohexane as a ligand are reported in U.S. Pat. No. 4,169,846 (Japanese Patent Laid-open No. 31648/1978) and Japanese Patent Laid-open Nos. 21697/1984, 34982/1985, 97991/1985, 109521/1985, and 59289/1987, and Japanese Patent Publication No. 29957/1983.

Cisplatin is commercially sold as an antitumor agent. However, it has a high toxicity to kidney and other organs, and thus a limitation is imposed to its use. In addition, its water solubility is so small that it can be administered only at an extremely low concentration. This has been a problem for curing diseases using this compound.

(1,2-diaminocyclohexane)malonatoplatinum (II), (1,2-diaminocyclohexane)methylmalonatoplatinum (II), and (1,2-diaminocyclohexane)ethylamalonatoplatinum (II) all disclosed in U.S. Pat. No. 4,169,846 are not necessarily satisfactory in their antitumor activities and water solubility.

Therefore, there has been a strong desire for a platinum complex having a superior antitumor activity and abundant water solubility, and yet possessing a lower degree of toxicity.

In view of this situation, the present inventors have synthesized various platinum complexes having 1,2-diaminocyclohexane as a ligand and studied their pharmaceutical effects, and found that platinum complexes having formula (I) hereinbelow had advantages of superior antitumor activity, abundant water solubility, and lower toxicity. Such findings have led to the completion of this invention.

SUMMARY OF THE INVENTION

Accordingly, an object of this invention is to provide a platinum complex having the formula (I):

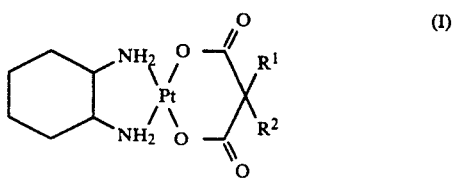

wherein $R^1$ and $R^2$ may be the same or different and each independently represents a methyl group or an ethyl group, and the configuration of 1,2-diaminocyclohexane is either cis-, trans-l-, trans-d-, or trans-dl-. Another object of the invention is to provide an antitumor agent comprising the above platinum complex as an effective component.

Other objects, features and advantages of the invention will hereinafter become more readily apparent from the following description.

DETAILED DESCRIPTION OF THE INVENTION AND PREFERRED EMBODIMENTS

The platinum complex (I) of this invention can be prepared, for example, according to the following reaction scheme:

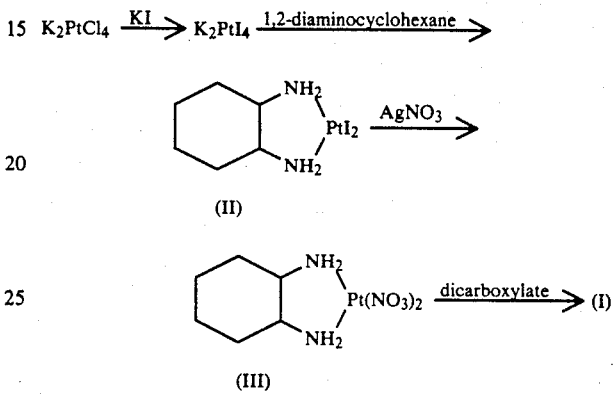

Specifically, according to the above reaction formulae, potassium iodide is added into an aqueous solution of potassium tetrachloroplatinate to produce an aqueous solution of potassium tetraiodoplatinate. To this solution 1,2-diaminocyclohexane is added and reacted to give the compound (II). This compound (II) in an aqueous solution is then treated with silver nitrate to prepare a dinitrato complex (III). The target compound (I) of this invention is prepared by reacting the dinitrato complex (III) with a dicarboxylate.

There are three types of stereoisomers and a racemic isomer for the ligand 1,2-diaminocyclohexane which is a raw material:

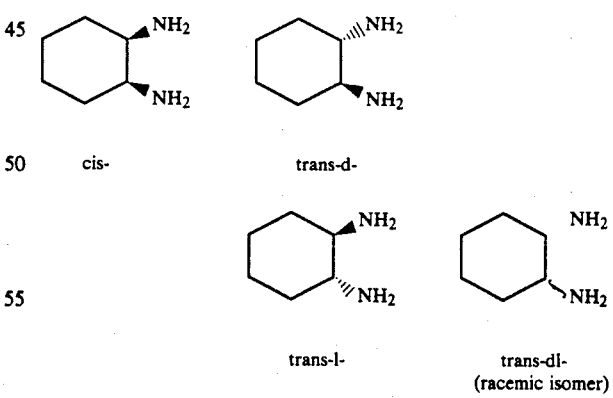

Accordingly, a desired platinum complex isomer can be prepared by using either of these stereoisomers or a racemic isomer of 1,2-diaminocyclohexane as a raw material. This invention includes all isomers having as a ligand all these types of stereoisomers or a racemic isomer of 1,2-diaminocyclohexane.

As shown in the examples described hereinbelow, the platinum complex of this invention exhibits an excellent antitumor activity and possesses high safety.

When the platinum complex of this invention is used as an antitumor agent, it is preferable that the platinum complex be administered orally at a dose of 1 to 50 mg, or parenterally at a dose of 0.5 to 18 mg, per 1 kg of the weight of a patient in a day, depending on the weight, the age, the sex, the physical condition, or the symptom of the patient or the way of administration.

An antitumor agent of this invention can be formed into various preparations, such as tablets, granules, powders, capsules, suspensions, injections, suppositories, or the like, according to known methods. Compound (I) of the present invention can be formed, according to known methods, into solid preparations for orally administrative use, including tablets, granules, powders, capsules, suppositories, or the like, by appropriately formulating excipients, and as required, binders, disintegrators, lubricants, coloring agents, sweetening agents, flavoring agents, fillers, coating agents, sugar-coating agents, and the like. Compound (I) of the present invention can be also formed, according to known methods, into preparations for subcutaneous, intravenous or intramuscular injection use by dissolving the compound (I) into solvents such as distilled water, physiological saline, 5% aqueous dextrose, aqueous ethanol, aqueous glycerol, aqueous propylene glycol, or the like. Preparations for suppositories of the compound (I) of this invention can be formed, according to known methods, by adding the compound (I) to base components such as cocoa butter or middle-chained fatty acid glycerol ester, followed by mixing them under heating. Among these preparations, injections are particularly preferable.

Other features of the invention will become apparent in the course of the following description of the exemplary embodiments which are given for illustration of the invention and are not intended to be limiting thereof.

EXAMPLES

EXAMPLE 1

Preparation of (trans-dl-1,2-diaminocyclohexane) dimethylmalonatoplatinum (II) (Compound No. 1)

200 ml of water was added to 20.76 g (0.05 mol) of potassium tetrachloroplatinate and 41.5 g (0.25 mol) of potassium iodide, and the mixture was stirred for 1 hour at room temperature. After completion of the reaction, the resultant reaction mixture was condensed to dryness in vacuo at 50° C. 200 ml of ethanol was added to the residue and the mixture was stirred, extracted with stirring and filtered. To the filtrate was added 5.7 g (0.05 mol) of trans-dl-1,2-diaminocyclohexane and the mixture was stirred at room temperature for 30 minutes. The deposited crystals were collected by filtration and washed with methanol and then with ether, and dried in vacuo to obtain 24.8 g of crystals of cis-diiodo(trans-dl-1,2-diaminocyclohexane) platinum (II) at a yield of 88%.

3.94 g (0.007 mol) of cis-diiodo(trans-dl-1,2-diaminocyclohexane) platinum (II) thus prepared was suspended int 200 ml of water and to the suspension was added 2.38 g (0.014 mol) of silver nitrate. The mixture was stirred at room temperature for 1 day. After reaction, the produced silver iodide was removed by filtration. To the filtrate a solution of 924 mg (0.007 mol) of dimethylmalonic acid in 11 ml of 1N sodium hydroxide was added and the mixture was left for 3 days at room temperature. The reaction mixture was condensed in vacuo and recrystallized in a water-methanol solvent to obtain 1.9 g of Compound No. 1 in a form of white crystals (yield: 62%).

m.p. 240°–255° C. (decomp.)
IR$\nu_{max}^{KBr}$ cm$^{-1}$: 3450, 3220, 3110, 1640, 1610
FAB-MS m/z: 440(M+H)$^+$
Elemental Analysis: for $C_{11}H_{20}N_2O_4Pt$

|  | C | H | N |
|---|---|---|---|
| Calculated (%) | 30.07 | 4.59 | 6.38 |
| Found (%) | 29.48 | 4.97 | 6.00 |

EXAMPLE 2

Preparation of (trans-dl-1,2-diaminocyclohexane) diethylmalonatoplatinum (II) (Compound No. 2)

1.9 g of Compound No. 2 in a form of white crystals was prepared in the same manner as in Example 1, except that 1.02 g of diethylmalonic acid was used instead of dimethylmalonic acid (yield: 58%).

m.p. 225°–240° C. (decomp.)
IR$\nu_{max}^{KBr}$ cm$^{-1}$: 3450, 3200, 3100, 1610, 1570
FAB-MS m/z: 468(M+H)$^+$
Elemental Analysis: for $C_{13}H_{24}N_2O_4Pt$

|  | C | H | N |
|---|---|---|---|
| Calculated (%) | 33.40 | 5.18 | 5.99 |
| Found (%) | 32.87 | 5.79 | 5.63 |

EXAMPLE 3

Preparation of (trans-l-1,2-diaminocyclohexane) dimethylmalonatoplatinum (II) (Compound No. 3)

The same procedures as in Example 1 were performed using trans-l-1,2-diaminocyclohexane instead of trans-dl-1,2-diaminocyclohexane to obtain Compound No. 3.

m.p. 240°–255° C. (decomp.)
IR $\nu_{max}^{KBr}$ cm$^{-1}$: 3450, 3220, 3110, 1640, 1610
FAB-MS m/z: 440(M+H)$^+$
Elemental Analysis: for $C_{11}H_{20}N_2O_4Pt$

|  | C | H | N |
|---|---|---|---|
| Calculated (%) | 30.07 | 4.59 | 6.38 |
| Found (%) | 29.77 | 4.78 | 6.01 |

EXAMPLE 4

Preparation of (trans-d-1,2-diaminocyclohexane) dimethylmalonatoplatinum (II) (Compound No. 4)

The same procedures as in Example 1 were performed using trans-dl-1,2-diaminocyclohexane instead of trans-dl-1,2-diaminocyclohexane to obtain Compound No. 4.

m.p. 240°–255° C. (decomp.)
IR $\nu_{max}^{KBr}$ cm$^{-1}$: 3450, 3220, 3110, 1640, 1610
FAB-MS m/z: 440(M+H)$^+$
Elemental Analysis: for $C_{11}H_{20}N_2O_4Pt$

|  | C | H | N |
|---|---|---|---|
| Calculated (%) | 30.07 | 4.59 | 6.38 |

-continued

|  | C | H | N |
|---|---|---|---|
| Found (%) | 29.85 | 4.88 | 5.99 |

EXAMPLE 5

Preparation of (cis-1,2-diaminocyclohexane) dimethylmalonatoplatinum (II) (Compound No. 5)

The same procedures as in Example 1 were performed using cis-1,2-diaminocyclohexane instead of trans-dl-1,2-diaminocyclohexane to obtain Compound No. 5.

m.p. 200°–220° C. (decomp)
IR $\nu_{max}^{KBr}$ cm$^{-1}$: 3450, 3220, 3110, 1640, 1610
FAB-MS m/z: 440(M+H)+
Elemental Analysis: for $C_{11}H_{20}N_2O_4Pt$

|  | C | H | N |
|---|---|---|---|
| Calculated (%) | 30.07 | 4.59 | 6.38 |
| Found (%) | 30.43 | 4.66 | 6.07 |

EXAMPLE 6

Preparation of (trans-l-1,2-diaminocyclohexane) diethylmalonatoplatinum (II) (Compound No. 6)

The same procedures as in Example 2 were performed using trans-l-1,2-diaminocyclohexane instead of trans-dl-1,2-diaminocyclohexane to obtain Compound No. 6.

m.p. 225°–240° C. (decomp.)
IR $\nu_{max}^{KBr}$ cm$^{-1}$: 3450 3220, 3100, 1610, 1570
FAB-MS m/z: 468(M+H)+
Elemental Analysis: for $C_{13}H_{24}N_2O_4Pt$

|  | C | H | N |
|---|---|---|---|
| Calculated (%) | 33.40 | 5.18 | 5.99 |
| Found (%) | 33.67 | 5.30 | 5.61 |

EXAMPLE 7

Preparation of (trans-d-1,2-diaminocyclohexane) diethylmalonatoplatinum (II) (Compound No. 7)

The same procedures as in Example 2 were performed using trans-d-1,2-diaminocyclohexane instead of trans-dl-1,2-diaminocyclohexane to obtain Compound No. 7.

m.p. 225°–240° C. (decomp.)
IR $\nu_{max}^{KBr}$ cm$^{-1}$: 3450, 3220, 3100, 1610, 1570
FAB-MS m/z: 468(M+H)+
Elemental Analysis for $C_{13}H_{24}N_2O_4Pt$

|  | C | H | N |
|---|---|---|---|
| Calculated (%) | 33.40 | 5.18 | 5.99 |
| Found (%) | 32.99 | 5.35 | 5.55 |

EXAMPLE 8

Preparation of (cis-1,2-diaminocyclohexane) diethylmalonatoplatinum (II) (Compound No. 8)

The same procedures as in Example 2 were performed using cis-1,2-diaminocyclohexane instead of trans-dl-1,2-diaminocyclohexane to obtain Compound No. 8.

m.p. 200°–215° C. (decomp.)
IR $\nu_{max}^{KBr}$ cm$^{-1}$: 3450, 3220, 3100, 1610, 1570
FAB-MS m/z: 468(M+H)+
Elemental Analysis: for $C_{13}H_{24}N_2O_4Pt$

|  | C | H | N |
|---|---|---|---|
| Calculated (%) | 33.40 | 5.18 | 5.99 |
| Found (%) | 33.01 | 5.48 | 5.61 |

EXPERIMENTAL EXAMPLES

Antitumor activity of the compound of this invention is now illustrated by experimental examples.

(Methods)

CDF$_1$ male mice (age: 6 weeks) consisting of 6 per each group were used to the test. $1 \times 10^5$ L1210 leukemia cells were intraperitoneally inoculated into each mouse. Test compounds dissolved in a solution of 0.5% CMC-Na in physiological saline were intraperitoneally administered to mice once a day for 5 consecutive days from the next day of the inoculation. A 0.5% CMC-Na solution in physiological saline was administered to the control group. Cisplatin, carboplatin, (trans-dl-1,2-diaminocyclohexane)-malonatoplatinum (II) (Comparative Compound a), (trans-dl-1,2-diaminocyclohexane)-methylmalonatoplatinum (II) (Comparative Compound b), (trans-dl-1,2-diaminocyclohexane)ethylmalonatoplatinum (II) (Comparative Compound c), were used as comparative compounds. All of these compounds are known compounds and Comparative Compounds a-c were disclosed in U.S. Pat. No. 4,169,846.

Observation was continued for consecutive 30 days after the administration. Increase life span (ILS) was determined according to the following equation:

$$ILS = (T/C - 1) \times 100 (\%)$$

wherein T is the mean survival days of the treated groups, and C is the mean survival days of the control groups.

The results are shown in Table 1.

TABLE 1

| Test Compounds | Dose (mg/kg) | ILS (%) | Survived ratio (%) |
|---|---|---|---|
| Compound No. 1 | 2.0 | 40 | 0 |
|  | 4.0 | 49 | 0 |
|  | 8.0 | above 136 | 17 |
|  | 16.0 | 112 | 0 |
|  | 32.0 | 130 | 0 |
| Compound No. 2 | 2.0 | 43 | 0 |
|  | 4.0 | 61 | 0 |
|  | 8.0 | above 135 | 33 |
|  | 16.0 | above 124 | 17 |
|  | 32.0 | above 168 | 33 |
| Cisplatin | 0.5 | 19 | 0 |
|  | 1.0 | 33 | 0 |
|  | 2.0 | 75 | 0 |
|  | 4.0 | 88 | 0 |
| Carboplatin | 8.0 | 27 | 0 |
|  | 16.0 | 29 | 0 |
|  | 32.0 | 43 | 0 |
|  | 64.0 | 70 | 0 |
|  | 128.0 | 25 | 0 |
| Comparative Compound a | 4.0 | 35 | 0 |
|  | 8.0 | 49 | 0 |
|  | 16.0 | 82 | 0 |
|  | 32.0 | 94 | 17 |
|  | 64.0 | above 108 | 17 |
| Comparative | 4.0 | 17 | 0 |

TABLE 1-continued

| Test Compounds | Dose (mg/kg) | ILS (%) | Survived ratio (%) |
|---|---|---|---|
| Compound b | 8.0 | 27 | 0 |
| | 16.0 | 43 | 0 |
| | 32.0 | 79 | 0 |
| Comparative Compound c | 4.0 | 27 | 0 |
| | 8.0 | 31 | 0 |
| | 16.0 | 52 | 0 |
| | 32.0 | 69 | 0 |

Therapeutic index of compounds of this invention was determined according to the following equation.

$$\text{Therapeutic Index} = \frac{LD_{50}}{ILS_{50}}$$

$ILS_{50}$: 50% increase life span dose (mg/kg)
$LD_{50}$: 50% lethal dose (mg/kg)
The greater the therapeutic index, the more effective the compound is. The results are shown in Table 2.

TABLE 2

| Test Compounds | $LD_{50}$ | $ILS_{50}$ | Therapeutic index |
|---|---|---|---|
| Compound No. 1 | 140.0 | 3.4 | 41.2 |
| Compound No. 2 | 140.0 | 2.7 | 51.9 |
| Cisplatin | 18.0 | 1.3 | 13.8 |
| Carboplatin | 200.0 | 31.2 | 6.4 |
| Comparative Compound a | 244.9 | 7.1 | 34.5 |
| Comparative Compound b | 312.6 | 14.9 | 21.0 |
| Comparative Compound c | 244.9 | 14.2 | 17.2 |

The water solubility of compounds of the present invention, cisplatin, and Comparative Compounds a-c are shown in Table 3.

TABLE 3

| Compounds | Water solubility (mg/ml) |
|---|---|
| Compound NO. 1 | 8 |
| Compound NO. 2 | 10 |
| Cisplatin | 1 |
| Comparative Compound a | 0.5 |
| Comparative Compound b | 0.1 |
| Comparative Compound c | 0.5 |

Preparation Example 1
Injection
<Formulation>

| Compound No. 1 | 20 mg |
|---|---|
| Distilling water | Balance |
| | 20 ml |

An injection was prepared using above ingredients according to a conventional method.

Preparation Example 2
Tablets
<Formulation>

| Compound No. 2 | 50 mg |
|---|---|
| Lactose | 50 mg |
| Crystallized cellulose | 50 mg |
| Corn starch | 30 mg |
| Hydroxypropyl cellulose | 18 mg |
| Magnesium stearate | 2 mg |
| Total | 200 mg |

The above ingredients were treated according to a conventional method to produce tablets. This formulation can also be used, as required, for preparing sugar-coating tablets or film coated tablets.

The compounds of this invention possess excellent antitumor activity with a high therapeutic index and abundant water solubility and thus are effective as an antitumor agent.

Obviously, numerous modifications and variations of the present invention are possible in light of the above teachings. It is therefore to be understood that within the scope of the appended claims, the invention may be practiced otherwise than as specifically described herein.

What is claimed is:

1. A platinum complex having the formula (I):

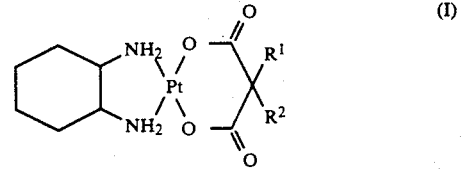

wherein $R^1$ and $R^2$ may be the same or different and each independently represents a methyl group or an ethyl group, and the configuration of 1,2-diaminocyclohexane is either cis-, trans-l-, trans-d-, or trans-dl-.

2. An antitumor agent comprising as an effective component a platinum complex having the formula (I):

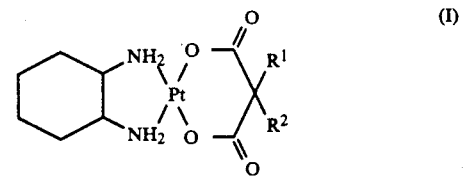

wherein $R^1$ and $R^2$ may be the same or different and each independently represents a methyl group or an ethyl group, and the configuration of 1,2-diaminocyclohexane is either cis-, trans-l-, trans-d-, or trans-dl-, in a therapeutically effective amount, mixed with an appropriate carrier.

* * * * *